US00PP36219P2

(12) United States Plant Patent
Jiang

(10) Patent No.: US PP36,219 P2
(45) Date of Patent: Oct. 22, 2024

(54) ***PELARGONIUM* PLANT NAMED 'PEQZ0105'**

(50) Latin Name: ***Pelargonium* x *interspecific***
Varietal Denomination: PEQZ0105

(71) Applicant: SYNGENTA CROP PROTECTION AG, Basel (CH)

(72) Inventor: Li Jiang, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/831,053

(22) Filed: May 21, 2024

(51) Int. Cl.
*A01H 5/02* (2018.01)
*A01H 6/42* (2018.01)

(52) U.S. Cl.
USPC ..... Plt./330
CPC ..... *A01H 6/425* (2018.05)

(58) Field of Classification Search
USPC ..... Plt./330
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named "PEQZ0105' particularly distinguished by rose colored inflorescences held above dark green foliage, on a spreading plant.

1 Drawing Sheet

Latin name of the genus and species of the plant claimed: *Pelargonium* x *interspecific*
Varietal denomination: 'PEQZ0105'

BACKGROUND OF THE NEW PLANT

The present invention comprises a new *Pelargonium*, botanically known as *Pelargonium interspecific*, and hereinafter referred to by the variety name 'PEQZ0105'.

'PEQZ0105' is a product of a planned breeding program. The new cultivar 'PEQZ0105' has rose colored single inflorescences held above dark green foliage, on a spreading plant habit.

'PEQZ0105' originates from a hybridization in a controlled breeding program made in March 2019 in a greenhouse in Amatitlán, Guatemala. The female parent was an unpatented, proprietary plant of *P. interspecific* parentage, identified as 'PEIBD1419-1V' with single lavender color florets and similar spreading habit and green foliage when compared to 'PEQZ0105'.

The male parent of 'PEQZ0105' was an unpatented, proprietary plant of *P. interspecific* parentage, identified as 'PEIBD1449-12V' with magenta-colored semi-double florets and a more vigorous mounding habit when compared to 'PEQZ0105'. The resultant seed was sown in September 2019.

'PEQZ0105' was selected as one flowering plant within the progeny of the stated cross in December 2019 in a greenhouse in Gilroy, California.

The first act of asexual reproduction of 'PEQZ0105' was accomplished when vegetative cuttings were propagated from the initial selection in February 2020 in a greenhouse in Gilroy, California.

BRIEF SUMMARY OF INVENTION

Horticultural examination of plants grown from cuttings of the plant initiated in August 2020 in Gilroy, California, and continuing thereafter, has demonstrated that the combination of characteristics as herein disclosed for 'PEQZ0105' are firmly fixed and are retained through successive generations of asexual reproduction.

'PEQZ0105' has not been observed under all possible environmental conditions. The phenotype may vary significantly with variations in environment such as temperature, light intensity, and day length.

A Plant Breeder's Right for this cultivar has not yet been applied for. 'PEQZ0105' has not been made publicly available more than one year prior to the filing of this application.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0105' with colors being as true as possible with an illustration of this type.

Figure 1:
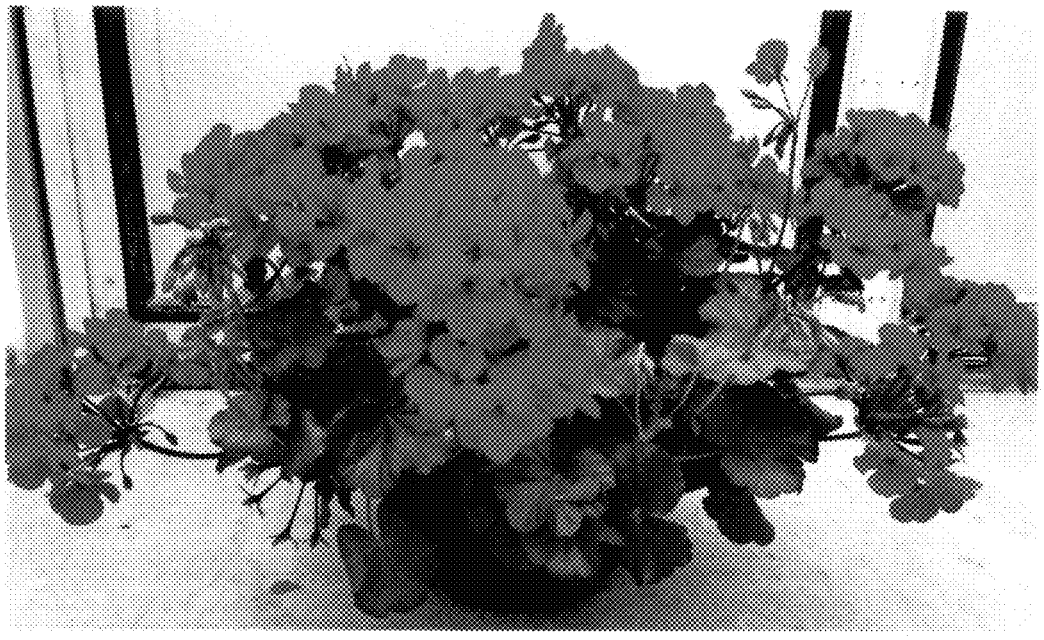
Figure 2:
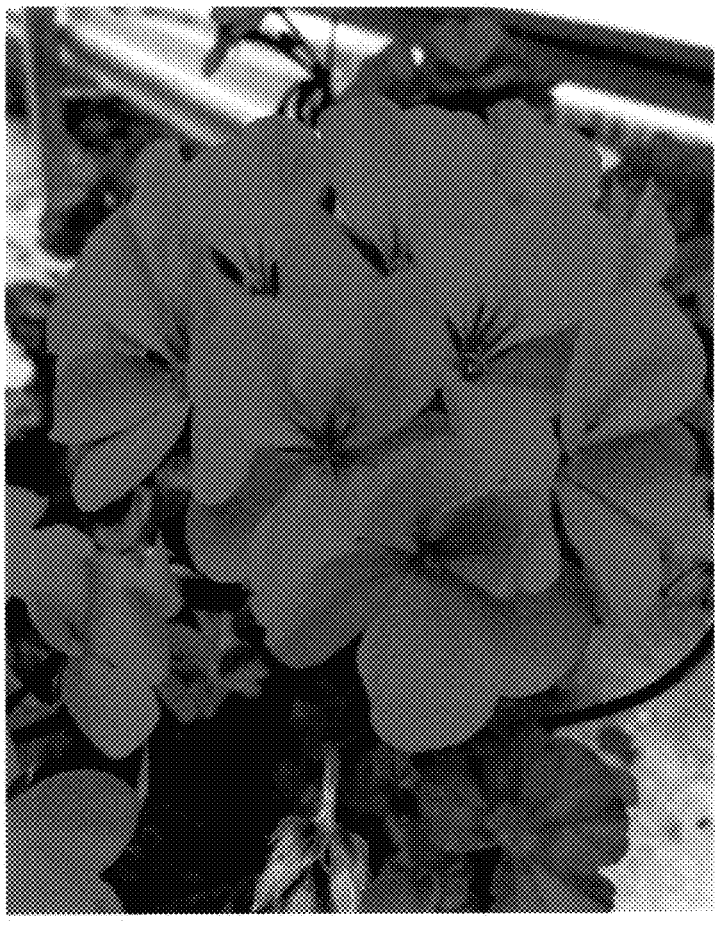

The photographic drawings show in FIG. 1, one flowering plants of the new variety and in FIG. 2, a close-up of an inflorescence.

DETAILED BOTANICAL DESCRIPTION

The plant descriptions and measurements were taken in Gilroy, California in April 2024 under natural light. These plants were approximately 17 weeks old and were grown in quart size pots, in a greenhouse trial. The plants shown in the photographs were about 17 weeks old growing in a quart pot in a greenhouse. The photographs were taken in April 2024.

Color references are made to The Royal Horticultural Society Colour Chart (RHS) of 2015.

TABLE 1

DIFFERENCES BETWEEN THE NEW VARIETY 'PEQZ0105' AND A MOST SIMILAR VARIETY

| | 'PEQZ0105' | Caldera Red 'PEI-AZ3193-01V' (not patented) |
|---|---|---|
| Color upper surface of petals: | Vivid purplish pink, RHS N66A | Vivid red, RHS 45B to RHS 46B |
| Peduncle diameter: | 0.3-0.5 cm | 0.2-0.3 cm |

PLANT

Form, growth and habit: Spreading growth habit.
Plant height: 26 cm.
Plant height (inflorescence included): 32-37 cm.
Plant width: 38 cm. (inflorescence included): 59 cm.

ROOTS

Number of days to initiate roots: 15-18 days at about 22 degrees C.
Number of days to produce a rooted cutting: 21-23 days at 22 degrees C.
Type: Fine, fibrous, free branching.
Color: RHS N155B but whiter.

FOLIAGE

Variegation: Absent.
Immature leaf, color upper surface: RHS NN137B.
Immature leaf, lower surface: RHS 137B.
Mature leaf, color upper surface: Between RHS 137A and RHS NN137A.
Mature leaf, color lower surface: Between RHS 137D and RHS NN137C.
Length: 5-6.5 cm.
Width: 7-9 cm.
Shape: Orbicular with irregular indents and wavy lobes.
Base shape: Orbicular and lobed.
Sinus of mature leaf: Wide.
Leaf base openness: Variable, immature leaves concave, mature leaves open.
Apex shape: Rounded.
Margin: Wavy, undulate margins.
Texture upper side: Hirsute.
Texture lower side: Hirsute.
Leaf zonation color: None.
Color of veins, upper surface: RHS 143B.
Color of veins, lower surface: Between RHS 146B and RHS 143C, distinct.
Pattern of veining: Palmate.
Petiole color: RHS 146B.
Petiole length: 4-10 cm.
Diameter of petiole: 0.2-0.3 cm.
Texture: Pilose, hirsute, glandular hairs.

STEM

Quantity of branches: 6-10.
Color of stem: Close to RHS 146B.
Anthocyanin coloration of stem: Anthocyanin coloration on top peduncles.
Length of stem: 9-27 cm.
Diameter: 0.5 cm.
Length of internodes: 1-4 cm.
Texture: Sparsely hirsute, pilose, glandular hairs.

PEDUNCLE

Color of peduncle: RHS 143C and RHS 183A.
Length of peduncle: 13-17 cm.
Peduncle diameter: 0.3-0.5 cm.
Texture: Hirsute, glandular hairs.
Anthocyanin coloration of peduncle: Some anthocyanin coloration.

PEDICEL

Color of pedicel: RHS 187A.
Length of pedicel: 2.5-4 cm.
Diameter of pedicel: 0.1-0.2 cm.
Texture: Sparsely pilose, glandular hairs.
Pedicel swelling: Swelling was not observed.

BUD (just before opening)

Color: Between RHS 144A and RHS 146A.
Length: 1.2-1.6 cm.
Width: 0.4-0.7 cm.
Shape: Elliptical.

INFLORESCENCE

Type: Umbel; semi-spherical or nearly semi-spherical.
Lastingness of individual flowers: 7-9 days at 18° C. temperature.
Number of inflorescences per plant: 8-15, with 5-12 immature umbels in various stages.
Average total number of buds: 18.
Fragrance: Mild.
Umbel diameter: 7-12 cm.
Umbel depth: 6-8 cm.

COROLLA

Form: Single.
Number of petals: 5.
Diameter of flower: 4.5-5.0 cm.
Depth of flower: 1-2 cm.
Side view shape: Concave.
Color upper petals, upper surface: RHS N66A.
Color upper petals, lower surface: RHS N66A.
Length of upper petals: 2.8-3.0 cm.
Width of upper petals: 1.8-2.0 cm.
Color lower petals, upper surface: RHS N66A.
Color lower petals, lower surface: RHS N57A.
Markings on upper petals: Yes, red purple veins RHS 61A on lower half of upper petal.
Markings on lower petals: Yes, red purple veins RHS 61A on lower half of lower petal.
Length of lower petals: 2.8-3.0 cm.
Width of lower petals: 1.8-2.0 cm.
Petal shape: Obovate to spathulate.
Apex shape: Rounded.
Margin: Entire.
Base: Attenuate.
Petal texture: Papillose on both surfaces.

CALYX

Number of sepals: 5.
Color of sepals: RHS 144A and RHS 59C.
Length of sepals: 1.1-1.5 cm.
Width of sepals: 0.2-0.6 cm.
Sepal shape: Lanceolate to linear.
Apex shape: Acute.
Margins: Mostly fused.
Texture, upper surface: Glandular hairs, hirsute.
Lower surface: Glandular hairs, hirsute.
Sepal flexing: Mostly unflexed sepals. Some might flex moderately.

REPRODUCTIVE ORGANS

GYNOECIUM

Pistil: RHS 67A.
Length: 0.7-1 cm.
Style color: RHS 67A.
Style length: 0.3 cm.
Stigma color: RHS 67A.
Ovary color: RHS 138C.
Ovary length: 0.4-0.5 cm.
Ovary diameter: 0.2 cm.

ANDROECIUM

Number of stamens: 5 with 2 staminodes.
Color of filaments: RHS 67A.
Length filaments: 0.7 cm.
Anther color: RHS 54A.
Length of anthers: 0.2-0.3 cm.
Color of pollen: RHS 171B.
Pollen amount: Some.
Fertility/Seed set: Has not been determined to date.
Disease/Pest resistance: Has not been determined to date.

What is claimed is:

1. A new and distinct variety of *Pelargonium* plant named 'PEQZ0105' substantially as illustrated and described herein.

* * * * *